United States Patent [19]

Klueppel et al.

[11] Patent Number: 5,145,665
[45] Date of Patent: Sep. 8, 1992

[54] PREPARATION FOR DENTAL AND ORAL HYGIENE CONTAINING POLYSACCHARIDE SPLITTING ENZYMES

[75] Inventors: Hans-Juergen Klueppel, Duesseldorf; Franz Foerg, Langenfeld, both of Fed. Rep. of Germany

[73] Assignee: Henkel Kommanditgesellschaft auf Aktien, Duesseldorf-Holthausen, Fed. Rep. of Germany

[21] Appl. No.: 730,941

[22] PCT Filed: Jan. 26, 1990

[86] PCT No.: PCT/EP90/00144
§ 371 Date: Aug. 1, 1991
§ 102(e) Date: Aug. 1, 1991

[87] PCT Pub. No.: WO90/08532
PCT Pub. Date: Aug. 9, 1990

[30] Foreign Application Priority Data

Feb. 4, 1989 [DE] Fed. Rep. of Germany ....... 3903348

[51] Int. Cl.$^5$ ...................... A61K 7/28; A61K 37/48; A61K 37/54
[52] U.S. Cl. ........................ 424/50; 424/49; 514/25; 514/901
[58] Field of Search ...................... 424/50; 514/25, 901

[56] References Cited

U.S. PATENT DOCUMENTS

| | | | |
|---|---|---|---|
| 4,748,158 | 5/1988 | Bierman et al. | 514/25 |
| 4,920,100 | 4/1990 | Lehmann et al. | 424/49 |
| 4,923,685 | 5/1990 | Wuelknitz et al. | 424/54 |

FOREIGN PATENT DOCUMENTS

| | | |
|---|---|---|
| 414128 | 2/1991 | European Pat. Off. |
| 3444958 | 6/1986 | Fed. Rep. of Germany. |
| 3725248 | 2/1989 | Fed. Rep. of Germany. |
| 01068312 | 3/1989 | Japan. |
| 3223209 | 10/1991 | Japan. |
| 9008532 | 8/1990 | World Int. Prop. O. |

OTHER PUBLICATIONS

Klueppel et al GA. 114(12): 108726c (1990) of PCT/WO 9008532 Aug. 9, 1990.
Wuelknitz et al GA. 115(6): 56974F (1991) of EP 414128 Feb. 27, 1991.
Sasaki et al GA. 111(18): 160022x (1989) of JPN 01068312 Mar. 14, 1989.
Wuelknitz et al. GA. 111(16): 1405245 (1989) of GER Off. DE 3725248 Feb. 9, 1989.
Biermann et al CA. 105(11): 94432D (1986) of Ger. Off DE 3444958 Jun. 12, 1986.

*Primary Examiner*—Shep K. Rose
*Attorney, Agent, or Firm*—Ernest G. Szoke; Wayne C. Jaeschke; Norvell E. Wisdom, Jr.

[57] ABSTRACT

Oral and dental care preparations containing polysaccharide-splitting enzymes, particularly dextranase, contain alkylglycosides, preferably those corresponding to the general formula $$RO-(C_6H_{10}O_5)_x-H,$$

in which R is an aliphatic radical of a primary $C_{8-22}$ fatty alcohol and $-(C_6H_{10}O_5)_x-H$ is an oligoglycoside group having an average degree of oligomerization x of 1 to 10 and preferably 1 to 3, as enzyme-compatible and high-foaming surfactants with good wetting properties.

13 Claims, No Drawings

PREPARATION FOR DENTAL AND ORAL HYGIENE CONTAINING POLYSACCHARIDE SPLITTING ENZYMES

BACKGROUND OF THE INVENTION

1. Field of the Invention

This invention relates to oral an dental care preparations containing polysaccharide-splitting enzymes and surfactants which do not damage these enzymes.

2. Statement of Related Art

Toothpastes, toothpowders and mouthwashes above all are used to care for the teeth, the gums and the oral cavity. These products normally contain surfactants to enhance the cleaning effect of the toothbrush and the abrasives present in toothpastes and toothpowders. In addition, oral and dental care preparations generally contain active substances for hardening the dental enamel and controlling tartar and plaque (bacterial coatings). It is known that dextrans, which are formed by bacterial polymerization from glucose, play an important part in the formation of plaque, so that it has repeatedly been proposed to add enzymes having a polysaccharide-splitting effect, particularly dextranase, to oral and dental care preparations to disrupt the mechanism responsible for the formation of plaque or to redissolve freshly formed coatings (cf. JADA, Vol. 82, Jan. 1971, 123-141, GB 1,202,629).

It is also known that many surfactants inhibit the effect of enzymes so that special surfactants more compatible with enzymes have already been proposed for use in oral and dental care preparations containing dextranase. According to GB 1,319,423, N-lauroyloxyethyl sulfoacetamide potassium salt is said to be compatible with dextranase. Many other patent applications propose stabilizing additives to protect the dextranase against damage by surfactants.

DESCRIPTION OF THE INVENTION

Objects of the Invention

The surfactants proposed hitherto, where they actually do show better compatibility with dextranase, have serious applicational disadvantages because foaming behavior is generally unsatisfactory or the wetting properties are inadequate. These disadvantages are largely eliminated by the oral and dental care preparations according to the invention.

SUMMARY OF THE INVENTION

The present invention relates to oral and dental care preparations containing (A) polysaccharide-splitting enzymes and (B) surfactants in an aqueous carrier, characterized in that alkylglycosides are present as the surfactants.

In the context of the invention, oral and dental care preparations are primarily understood to be toothpastes and mouthwashes containing an aqueous carrier. However, the preparations according to the invention also include toothpowders because toothpowders are regularly used with water and, accordingly, also require water as carrier component in use.

Polysaccharide-splitting enzymes are understood to be any carbohydrases which catalyze the enzymatic hydrolysis of carbohydate constituents. Enzymes such as these are obtained from microorganisms by known processes.

DESCRIPTION OF PREFERRED EMBODIMENTS

Examples of suitable enzymes are $\alpha$- and $\beta$-glucosidas-es, $\alpha$- and $\beta$-galactosidase, $\alpha$- and $\beta$-amylase, glucoamylase ($\alpha$-1,4-glucanglucohydrolase), cellulase, saccharase, mutanase and dextranase. It is particularly preferred to use dextranase (1,6-$\alpha$-D-glucan-6-glucanohydrolase) and/or 1,3-glucanase as the polysaccharide-splitting enzyme.

Alkylglycosides, their production and their use as surfactants are known, for example, from U.S. Pat. Nos. 3,839,318, 3,707,535 and 3,547,828, DE-A-1,943 689, DE-A-2 036 472 and DE-A-3 001 064 and from EP-A-77 167. They are produced in particular by reaction of glucose or oligosaccharides with primary $C_{8-22}$ alcohols. So far as the glycoside part is concerned, both monoglycosides, in which a cyclic sugar residue is attached to the fatty alcohol by a glycosidic bond, and oligomeric glycosides having a degree of polymerization of preferably up to 10 are suitable. Preferred alkylglycosides for the production of the preparations according to the invention are those corresponding to the general formula $RO-(C_6H_{10}O_5)_x-H$, in which R is an aliphatic radical of a primary $C_{8-22}$ fatty alcohol and $-(C_6H_{10}O_5)_x-H$ is an oligoglucoside group having an average degree of oligomerization x of 1 to 10. Particularly preferred oligoglucosides corresponding to the above general formula are those in which R is an aliphatic, linear $C_{10-16}$ alkyl radical and $-(C_6H_{10}O_5)_x-H$ is an oligoglucoside group having an average degree of oligomerization x of 1 to 3. The average degree of oligomerization is derived from the molar components of the individual oligomers by dividing the sum of the structural units by the sum of the molecules (cf. *Principles of Polymer Chemistry*, Paul J. Flory, Cornell University Press, Ithaca, N.Y., 1953, pages 36-37).

The oral and dental care preparations according to the invention contain the polysaccharide-splitting enzymes in quantities of 100 to 20,000 units per g of the dental care preparation, one unit corresponding to the quantity of enzyme which, on incubation with a degradable polysaccharide, for example with dextran, brings about the formation of 1 $\mu$g glucose per minute. The polysaccharide-splitting enzymes are preferably present in the oral and dental care preparations in such quantities that, in a single application, approximately 2,500 to 30,000 units of the enzyme enter the oral cavity. Where a dextranase preparation containing 200,000 to 2,000,000 units per g are used, this represents an addition of 0.05 to 3.0% by weight to toothpastes and mouthwashes. The alkylglycosides are preferably present in the oral and dental care preparations according to the invention in a quantity of 0.1 to 5% by weight. Accordingly, where the usual, approximately 50% aqueous alkylglucoside preparations are used, quantities of about 0.2 to 10% by weight of these alkylglucoside preparations have to be used. In mouthwash concentrates which are diluted before use, higher concentrations have to be used in accordance with the intended dilution ratio.

In addition to the characteristic, polysaccharide-splitting enzymes and the alkylglycosides, the oral and dental care preparations according to the invention contain the aqueous carriers typical of the particular formulation.

In the case of mouthwashes, the carrier normally consists of an aqueous or aqueous-ethanolic solution of ethereal oils, astringent and tonic drug extracts, caries-inhibiting additives, for example sodium fluoride or monofluorophosphate, tartar-inhibiting additives, for example organophosphonates, such as 1-hydroxyethane-1,1-diphosphonic acid, phosphonopropane-1,1,3-tricarboxylic acid or 1-azacycloheptane-1,1-diphosphonic acid or water-soluble salts thereof, and optionally sweeteners.

In the case of toothpastes or toothcreams, the carrier generally consists of paste-like preparations of water, viscosity regulators, humectants, abrasives or polishes, sweeteners, flavorings, deodorizing agents and agents active against mouth and tooth disease. The toothpastes according to the invention may contain any of the usual polishing substances, such as for example chalk, dicalcium phosphate, insoluble sodium metaphosphate, aluminium silicates, calcium pyrophosphate, finely divided synthetic resins, silicas, aluminium oxide and aluminium oxide trihydrate.

Preferred polishing substances for the toothpastes according to the invention are, above all, finely divided xerogel silicas, hydrogel silicas, precipitated silicas, aluminium oxide trihydrate and finely divided α-aluminium oxide or mixtures of these polishing substances in quantities of 15 to 40% by weight of the toothpaste.

Suitable humectants are, for example, glycerol, sorbitol, xylitol, propylene glycols, polyethylene glycols, particularly those having average molecular weights of 200 to 800. Suitable viscosity regulators (or binders) are, for example, natural and/or synthetic water-soluble polymers, such as carragheenates, tragacanth, starch and starch ethers, cellulose ethers, such as for example carboxymethyl cellulose (Na salt), hydroxyethyl cellulose, methyl hydroxypropyl cellulose, guar, acacia gum, agar agar, xanthan gum, carob bean flour, pectins, water-soluble carboxyvinyl polymers (for example Carbopol ® types), polyvinyl alcohol, polyvinyl pyrrolidone, polyethylene glycol, particularly types having molecular weights of 1,500 to 1,000,000.

Other suitable viscosity regulators are, for example, layer silicates such as, for example, montmorillonite clays, colloidal thickening silica, such as for example aerogel silica or pyrogenic silicas. A particularly suitable carrier for the production of toothpastes containing the enzyme/alkylglycoside combination according to the invention contains, for example, 20 to 35% by weight water, 20 to 35% by weight sorbitol, 5 to 15% by weight glycerol, 2 to 10% by weight polyethylene glycol (average molecular weight 200 to 800), 0.1 to 0.5% by weight carboxymethyl cellulose, 1 to 3% by weight thickening silica and 14 to 40% by weight abrasives and polishes.

Other typical toothpaste additives are
preservatives and antimicrobial agents, such as for example p-hydroxybenzoic acid methyl, ethyl or propyl ester, sodium sorbate, sodium benzoate, bromochlorophene, phenyl salicylic acid ester, thymol, etc.
anti-tartar agents, for example organophosphonates, such as the sodium salts of 1-hydroxyethane-1,1-diphosphonic acid, 1-azacycloheptane-1,1-diphosphonic acid, 1-phosphonopropane-1,2,3-tricarboxylic acid and other phosphonic acids of the type known, for example, from US-PS 3,488,419, DE-OS 22 24 430 and DE-OS 23 43 196,
caries inhibitors, such as for example sodium fluoride, sodium monofluorophosphate, tin fluoride,
sweeteners, such as for example saccharin sodium, sodium cyclamate, sucrose, lactose, maltose, fructose,
flavorings, such as for example peppermint oil, spearmint oil, eucalyptus oil, aniseed oil, fennel oil, caraway oil, menthyl acetate, cinnamaldehyde, anethol, vanillin, thymol and mixtures of these and other natural and synthetic flavorings,
pigments, such as titanium dioxide for example,
dyes,
buffers, such as for example primary, secondary or tertiary alkali phosphates or citric acid/sodium citrate,
wound-healing and inflammation-inhibiting agents, such as for example allantoin, urea, azulene, chamomile active substances, or acetyl salicylic acid derivatives.

The alkylglycosides to be used in accordance with the invention are preferably the only surfactants present in the oral and dental care preparations. However, the oral and dental care preparations according to the invention may contain certain nonionic surfactants which also do very little damage to the polysaccharide-degrading enzymes. The nonionic surfactants in question, which may be useful in solubilizing flavor components, are for example ethoxylated fatty acid glycerides, ethoxylated fatty acid sorbitan partial esters or fatty acid partial esters of glycerol or sorbitan ethoxylates. Solubilizing nonionic surfactants such as these may optionally be present in the carrier—in addition to the alkylglycosides—in a quantity of 0.01 to 0.3% by weight, based on the preparation as a whole.

The invention is illustrated by the following Examples.

EXAMPLES

1. Testing of compatibility between surfactants and polysaccharide-splitting enzymes

1.1 Principle of measurement

The activity and activity loss of polysaccharide-splitting enzymes under the effect of surfactants was determined by way of example on 1,6-α-D-glucan-6-glucanohydrolase by measuring the release of glucose from a dextran solution under the effect of the enzyme and of surfactants over predetermined periods. The quantity of glucose released was determined by UV-spectrometry using 3,5-dinitrosalicylic acid (which is reduced by the aldehyde function of the glucose to an orange-red colored compound—probably 3-amino-5-nitrosalicylic acid).

1.2 Procedure

1 Portion dextranase (1,6-α-D-glucan-6-glucanohydrolase; Enzyme Catalog EC 3.2.1.11, Sigma), order no. D 1508, 100 units, was dissolved in 1 ml phosphate buffer solution (pH 7). 10 μl of this solution were mixed with 0.5 ml of the surfactant solution (2% by weight surfactant in water) and stored for the predetermined time.

Control of enzyme activity: After equilibration for 5 minutes in a water bath at 35° C., 1 ml of a 1% solution of dextran (Sigma, D 5376, molecular weight 2,000,000) was added. After 15 minutes at 35° C., 2 ml "DNS Reagent" (for composition, see under 1.3) were added.

The solution was then heated for 15 minutes to 100° C., cooled under running water to approximately 20° C. and made up to 10 ml with distilled water. After another 30 minutes, the UV absorption was measured at a wavelength of 530 nm. From the calibration curve recorded after reaction of glucose solutions of known concentration with "DNS Reagent", it was possible to determine the quantity of glucose released and hence the activity of the enzyme.

1.3 Composition of the "DNS Reagent"

15 g 3,5-dinitrosalicylic acid (DNS) were dissolved in 800 ml softened water and 300 ml 4.5% sodium hydroxide solution added to the resulting solution. 225 g potassium sodium tartrate were dissolved in this solution, after which 69 g phenol solution (10 g phenol and 22 ml 10% sodium hydroxide solution made up to 100 ml with softened water) and 6.9 g sodium hydrogen carbonate were added. The solution thus obtained was left standing for 48 hours, subsequently filtered and stored in darkness.

1.4 Result

For the surfactants
(1) Na lauryl sulfate
(2) ceotstearyl alcohol (30:70) polyglycol ether (25 mol EO)
(3) Di-Na sulfosuccinic acid monolaurate
(4) protein hydrolyzate fatty acid condensation product (Na salt) and
(5) alkyl (C12/C14 = 70:30)-oligo (x=1.2)-glucoside
the following enzyme activities were measured after 1 hour, 1 week and 4 weeks:

| Surfactant | 1 hour | 1 week | 4 weeks |
|---|---|---|---|
| Standard (surfactant-free) | 640 | 570 | 560 |
| (1) | 230 | 0 | 0 |
| (2) | 575 | 620 | 285 |
| (3) | 525 | 415 | 250 |
| (4) | 790 | 620 | 330 |
| (5), invention | 610 | 675 | 500 |

2. Formulation Examples

| | Quantities in % by weight |
|---|---|
| Tooth cream | |
| Na carboxymethyl cellulose | 1.10 |
| Glycerol, 86% | 10.00 |
| Sorbitol, 70% | 15.00 |
| Saccharin sodium | 0.05 |
| Sodium cyclamate | 0.10 |
| Sodium monofluorophosphate | 1.14 |
| PHB methyl ester | 0.15 |
| Flavouring | 1.00 |
| Calcium hydrogen phosphate dihydrate | 25.00 |
| Calcium hydrogen phosphate, anhydrous | 7.00 |
| Silicon dioxide, highly disperse | 2.00 |
| Alkylglucoside | 1.50 |
| Dextranase (1,000,000 units per g) | 0.45 |
| Water | ad 100 |
| Gel toothcream | |
| Na carboxymethyl cellulose | 0.40 |
| Sorbitol, 70% | 72.00 |
| Polyethylene glycol 1500 | 3.00 |
| Saccharin sodium | 0.07 |
| Sodium fluoride | 0.24 |
| PHB ethyl ester | 0.15 |
| Flavouring | 1.10 |
| Abrasive silica | 11.00 |
| Thickening silica | 6.00 |
| Alkylglucoside | 1.40 |
| Dextranase (1,000,000 units per g) | 0.50 |
| Water | ad 100 |
| Toothpowder | |
| Na carboxymethyl cellulose | 1.50 |
| Polyethylene glycol 1500 | 4.00 |
| Saccharin sodium | 0.30 |
| Flavouring | 1.40 |
| Silicon dioxide, highly disperse | 3.50 |
| Calcium carbonate, precipit. | 77.50 |
| Alkylglucoside | 1.40 |
| Dextranase (1,000,000 units per g) | 0.40 |
| Mouthwash | |
| Ethanol, 96% by volume non-denatured | 5.00 |
| Sorbitol, 70% | 3.00 |
| Saccharin sodium | 0.07 |
| PHB methyl ester | 0.10 |
| Flavouring | 0.15 |
| Alkylglucoside | 0.70 |
| Dextranase (1,000,000 units per g) | 0.12 |
| Water | ad 100 |

What is claimed is:

1. Oral and dental care preparations containing (A) polysaccharide-splitting enzymes and (B) surfactants in an aqueous carrier, wherein the improvement comprises the presence of alkylglycosides as the surfactants.

2. Oral and dental care preparations as claimed in claim 1, containing dextranase or 1,3-glucanase as the polysaccharide-splitting enzymes.

3. Oral and dental care preparations as claimed in claim 2 which contain as surface-active alkylglycosides those corresponding to the general formula RO—$(C_6H_{10}O_5)_x$—H, in which R is an alilphatic radical of a primary $C_{8-22}$ fatty alcohol and —$(C_6H_{10}O_5)_x$—H is an oligoglycoside group having an average degree of oligomerization x of 1 to 10.

4. Oral and dental care preparations as claimed in claim 3, wherein R is an aliphatic, linear $C_{10-16}$ alkyl radical and —$(C_6H_{10}O_5)_x$—H is an oligoglucoside group having an average degree of oligomerization x of 1 to 3.

5. Oral and dental care preparations as claimed in claim 4 that are selected from the group consisting of mouthwashes in the form of an aqueous or aqueous-ethanolic solution containing flavorings and toothpastes in the form of an aqueous dispersion of abrasives and polishes containing thickeners, humectants and flavorings.

6. Oral and dental care preparations as claimed in claim 1 which contain as surface-active alkylglycosides those corresponding to the general formula RO—$(C_6H_{10}O_5)_x$—H, in which R is an aliphatic radical of a primary $C_{8-22}$ fatty alcohol and —$(C_6H_{10}O_5)_x$—H is an oligoglycoside group having an average degree of oligomerization x of 1 to 10.

7. Oral and dental care preparations as claimed in claim 6, wherein R is an aliphatic, linear $C_{10-16}$ alkyl radical and —$(C_6H_{10}O_5)_x$—H is an oligoglucoside group having an average degree of oligomerization x of 1 to 3.

8. Oral and dental care preparations as claimed in claim 7 that are selected from the group consisting of mouthwashes in the form of an aqueous or aqueous-ethanolic solution containing flavorings and toothpastes in the form of an aqueous dispersion of abrasives and polishes containing thickeners, humectants and flavorings.

9. Oral and dental care preparations as claimed in claim 6 that are selected from the group consisting of mouthwashes in the form of an aqueous or aqueous-ethanolic solution containing flavorings and toothpastes in the form of an aqueous dispersion of abrasives and polishes containing thickeners, humectants and flavorings.

10. Oral and dental care preparations as claimed in claim 5 that are selected from the group consisting of mouthwashes in the form of an aqueous or aqueous-ethanolic solution containing flavorings and toothpastes in the form of an aqueous dispersion of abrasives and polishes containing thickeners, humectants and flavorings.

11. Oral and dental care preparations as claimed in claim 3 that are selected from the group consisting of mouthwashes in the form of an aqueous or aqueous-ethanolic solution containing flavorings and toothpastes in the form of an aqueous dispersion of abrasives and polishes containing thickeners, humectants and flavorings.

12. Oral and dental care preparations as claimed in claim 2 that are selected from the group consisting of mouthwashes in the form of an aqueous or aqueous-ethanolic solution containing flavorings and toothpastes in the form of an aqueous dispersion of abrasives and polishes containing thickeners, humectants and flavorings.

13. Oral and dental care preparations as claimed in claim 1 that are selected from the group consisting of mouthwashes in the form of an aqueous or aqueous-ethanolic solution containing flavorings and toothpastes in the form of an aqueous dispersion of abrasives and polishes containing thickeners, humectants and flavorings.

* * * * *